United States Patent [19]

Lenz

[11] 4,389,345

[45] Jun. 21, 1983

[54] 3-OXOESTRA-17-ACETONITRILE AND UNSATURATED ANALOGS

[75] Inventor: George R. Lenz, Glenview, Ill.

[73] Assignee: G.D. Searle & Co., Skokie, Ill.

[21] Appl. No.: 310,204

[22] Filed: Oct. 9, 1981

[51] Int. Cl.³ ............................................. C07J 7/00
[52] U.S. Cl. ............................ 260/397.1; 260/397.3; 260/397.5
[58] Field of Search ................ 260/397.1, 397.3, 397.5

[56] References Cited

U.S. PATENT DOCUMENTS 3,960,842  6/1976  Haffer et al. ............... 260/239.55 C

OTHER PUBLICATIONS

Pettit et al., J. Org. Chem. 1971, 36(21) pp. 3207-3211, as found in Chem. Abstract (1971) vol. 75, 151, 969x.

Primary Examiner—Elbert L. Roberts
Attorney, Agent, or Firm—James G. Passé

[57] ABSTRACT

This invention relates to cyano steroids of formula I. These compounds exhibit progestational activity.

15 Claims, No Drawings

3-OXOESTRA-17-ACETONITRILE AND UNSATURATED ANALOGS

BACKGROUND OF THE INVENTION

The invention relates to certain novel cyano steroids. In particular, the invention relates to novel cyano steroids of formula 1 which exhibit progestational activity.

Compounds, particularly steroids, which exhibit progestational activity are widely known in the art. Both naturally occurring and synthetic compounds of this type are well known, for example, progesterone and ethisterone respectively. Such compounds are useful in treating functional uterine bleeding, dysmenorrhea, and endometriosis. For a detailed discussion of progestins see, for example, Goodman and Gilman, The Pharmacological Basis of Thereapeutics 4th pps. 1550–1557 (1970). See also, for example, U.S. Pat. No. 3,812,166.

PRIOR ART

Steroids with progestational activity are widely known as discussed above. In particular certain cyanosteroids are known. For example,
3-(acetyloxy) pregna-5,17(20)-diene-21-nitrile is described in Chem. Abstracts 618365h,
3-oxo-pregn-4-ene-21-nitrile is described in Chem. Abstracts 75151969x, and
3-(acetyloxy)pregn-5-ene-21-nitrile is described in Index Chem. 1485996.

SUMMARY OF THE INVENTION

The invention particularly provides a compound according to Formula I:
wherein $R_1$ is:
  (a) hydrogen;
  (b) $H_2$; or
  (c) $COOR_2$;
wherein $R_2$ is:
  (a) hydrogen; or
  (b) alkyl of one to six carbon atoms, inclusive; or
  (c) aralalkyl of four to thirteen carbon atoms, inclusive;
wherein $R_3$ is:
  (a) oxo;
  (b) =NOH; or
  (c) $-OR_4$;
  (d) $-OC=O(R_4)$
wherein $R_4$ is:
  (a) hydrogen; or
  (b) alkyl of one to six carbon atoms, inclusive;
with the proviso that $R_1$ may not be hydrogen or $H_2$ when $R_3$ is oxo or when $R_3$ is —OAcetyl.

Examples of alkyl of one to six carbon atoms, inclusive, are methyl, ethyl, propyl, butyl, pentyl and hexyl and the isomeric forms thereof.

Examples of aralalkyl of four to thirteen carbon atoms, inclusive, are where the alkyl portion is from one to six carbon atoms inclusive as described above and the aryl portion is a cyclic compound from 3 to 7 atoms inclusive; examples include cyclopropyl methyl, cyclopropyl ethyl, cyclopropyl propyl, cyclopropyl butyl, cyclopropyl pentyl, cyclopropyl hexyl, cyclobutyl methyl, cyclobutyl ethyl, cyclobutyl propyl, cyclobutyl butyl, cyclobutyl pentyl, cyclopropyl hexyl, cyclopentyl methyl, cyclopentyl ethyl, cyclopentyl propyl, cyclopentyl butyl, cyclopentyl pentyl, cyclopentyl hexyl, cyclohexyl methyl, cyclohexyl ethyl, cyclohexyl propyl, cyclohexyl butyl, cyclohexyl pentyl, cyclohexyl hexyl, cycloheptyl methyl, cycloheptyl ethyl, cycloheptyl propyl, cycloheptyl butyl, cycloheptyl pentyl, cycloheptyl hexyl, benzyl methyl, benzyl ethyl, benzyl propyl benzyl butyl, benzyl pentyl, benzyl hexyl, and the other saturated, unsaturated, partially saturated and isomeric forms thereof.

The test procedure used to determine progestational activity is as follows:

Immature, intact female rabbits, are primed with 5 micrograms of estradiol-17-$\beta$ daily for 6 days. The uterus is the organ involved in this exam with histological examination of the uterine endometrium being preformed. An initial screening dose of the test compound of 1/mg/kg is administered subcutaneously, bucally or intragastrically with the dosage adjusted as necessary. All test compounds are run against progesterone as a standard.

The degree or arborization of the lumenal epithelium of the uterus is graded from +1 to +4. An average rating of +2 represents minimal activity (produced by progesterone subcutaneously at 0.05 mg/day) while an average rating of +3.5 to +4.0 represents maximal activity (produced by progesterone subcutaneously at 0.1 mg/day). Unless stated to the contrary, potency estimates will be made by comparing doses of the standard and test compound that produce minimal activity.

Aborization (proliferation) of glandular epithelium in estrogen primed rabbits is brought about by progesterone. Progesterone, or a functional corpus luteum, is a factor in normal uterine development in the menstrual cycle and maintenance of pregnancy. Development and function of mammary tissue is also influenced by progestins. Concurrently with this test, endocrinal carbonic anhydrase is determined, an increase in which indicates progestational activity, as shown by Miyake, et al, Endocrinology, 63 816 (1958).

By virtue of this progestational activity the compounds of formula I are useful in treating functional uterine bleeding, dysmenorrhea and endometriosis. The compounds can be administered in such oral unit dosage forms such as tablets, capsules, pills, powders, or granules. They also may be administered rectally, vaginally in such forms as suppositories; they may also be introduced in the form of eye drops, interparenterally, subcutaneously, or intramuscularly, using forms known to the pharmaceutical art. In general, the preferred form of administration is orally.

An effective but non-toxic quantity of the compound is employed in treatment. The dosage regimen for preventing or treating symptoms by the compounds of this invention is selected in accordance with a variety of factors including the type, age, weight, sex, and medical condition of the mammal, the severity of the symptoms, the route of administration and the particular compound employed.

Initial dosages of the compounds of the invention are ordinarily in the area of 1 mg/kg up to at least 50 mg/kg orally. When other forms of administration are employed, equivalent doses are administered. When dosages beyond 50 mg/kg are employed, care should be taken with each subsequent dose to monitor possible undesirable effects.

The compounds of this invention may be administered in a suitable hydrated form.

The compounds of the invention are prepared according to the following general procedures.

To a solution of a sodium salt of diethylcyanomethylene phosphonate in a suitable solvent like tetrohydrofuran or 1,2-dimethoxyethane is added a 19-norandrostene-3,17-dione with the 3 ketone suitably protected as in enol ether, a dimethoxy ketal or an ethylenedioxyl ketal. After a suitable contact time, the reaction mixture is poured into water and the protected 7 cyanomethylene steroid collected. The protecting group is removed by warming an aqueous alcohol preferably methanol or ethanol, with an acid such as citric, p-toluenesulfonic or hydrochloric. Upon regeneration of the 3-ketone, the steroid is isolated by dilution with water. For example, one part of the 3-enol ether of 19-nor-androstene-3,17-dione(C. DJERASSI, et al J.AMER.CHEM.SOC. 76, 4092(1954)) in 2.5 parts of 1,2-dimethoxyethane is added to 40 parts of a solution of the sodium salt of diethylcyanomethylene phosphonate in the same solvent. After heating to reflux for an appropriate time, the resultant mixture is poured into about 500 parts of water and the enol ether collected and dried. One part of the enol ether may be dissolved by heating in 200 parts of methanol and 25 parts of distilled water. One part of p-toluenesulfonic acid has been added. After about 15 minutes the solution is diluted with water and then the deprotected ketone is obtained.

To prepare 3-hydroxy steroids the invention, a solution of the sodium salt of diethylcyanomethylene phosphonate and a suitable solvent such as tetrahydrofuran or 1,2-dimethoxyethane, is added a 3-hydroxy-19-norandrost-5-ene-17-ketone with the 3-alcohol suitably protected as a tetrahydropyranyl ether, a trialkylsilyl ether or a tetrahydrofuranyl ether. After a suitable contact time, the reaction mixture is poured into water and the protected 7-cyanomethylene steroid is collected. The protecting group may be removed by treatment with an acid such as p-toluenesulfonic, hydrochloric or citric, in an aqueous alcohol, or with a fluoride anion if the protecting group is trialkylsilyl. The resultant 3-hydroxy-5-en-steroids may be oxidized to the conjugated enone by means of the OPPENAUER reaction. (For example see U.S. Pat. No. 3,597,418).

To prepare 3-β hydroxy steroids of the invention, a mixture of 3β-hydroxy-19-nor-androst-5-ene-17-ketone with the hydroxyl group protected with an acyl or aroyl group is added 4 parts of acetic acid, 4 parts of benzyl cyanoacetate and 3 parts of ammonium acetate and 15 parts of benzene. After a suitable reflux period, the mixture is diluted with additional solvent and the mixture washed with water. After drying the organic solution with a suitable drying agent, such as sodium sulfate, magnesium sulfate, or calcium chloride, the solvent is removed and the resultant cyano acrylate steroid crystalized from a suitable solvent. After dilution with additional solvent, the mixture is washed with water the organic layer dried with sodium sulfate or other appropriate material and evaporated.

DESCRIPTION OF THE PREFERRED EMBODIMENTS

The invention can be more fully understood by the following examples. The example compound structures are represented on Charts A through E as well as the schematic order of production.

EXAMPLE 1

3-Ethoxy-19-Norprega-3,5,17(20)-Triene-21-Nitrile

To a suspension of 3.5 parts of sodium hydride and 25 parts of dry 1,2-dimethoxyethane is added 14.5 parts of diethylcyanomethylene phosphonate in 15 parts of the same solvent. After hydrogen evolution ceases, 20 parts of the enol ether of 19-norandrostenedione in 50 parts of warm 1,2 dimethoxyethane is added. The solution is refluxed for 2 hours and poured into 500 parts of distilled water. After crystallization is complete, the title compound is filtered and air dried.

EXAMPLE 2

3-Oxo-19-Norpregna-4,17(20)-Diene-Nitrile

One part of the title compound of Example 1 is dissolved by heating in 200 parts of methanol and 25 parts of distilled water. Then one part of p-toluenesulfonic acid monohydrate is added. After 15 minutes the solution is poured into water and the title compound is collected which has a melting point of 147 to 149.5 degrees centigrade.

EXAMPLE 3

3-Hydroxy-19-Norpregna-5,17(20)-Diene-21-Nitrile

To a suspension of 1.25 parts of sodium hydride and 50 parts of tetrahydrofuran is added 9.3 parts of diethylcyanomethylene phosphonate is 25 parts of the same solvent. After hydrogen evolution ceases, 5.5 parts of the tetrahydropyranyl ether of 19-nor-dehydroisoandrosterone in 25 parts of the same solvent is added. After standing at room temperature for 16 hours, the reaction mixture is diluted with 350 parts of water and the precipitated product collected.

The crude product is then suspended in 300 parts of ethanol and 1.5 parts of p-toluenesulfonic acid monohydrate is added. After stirring for 16 hours, the solution is diluted with 800 parts of water. The title product is collected having a melting point of 104° to 108° C. The title product may then be dissolved in 100 parts of toluene and 2 parts of N-methyl-4-piperidone and 2 parts of aluminum isopropoxide added. After refluxing for 3 hours the reacting mixture is cooled and washed with hydrochloric acid. The toluene solution is dried over sodium sulfate and evaporated to yield the title compound of Example 2 after recrystallization from an acetone water solvent system.

EXAMPLE 4

3-Acetyloxy-19-Norpregna-5,17(20)-Diene-21-Nitrile

To a solution of 3 parts of sodium diethylcyanomethylene phosphonate in 25 parts of tetrahydrofuran is added 1 part of 19-nor-dehydroisoandrostrone acetate. After stirring at room temperature for 16 hours, the solution is diluted with 225 parts of distilled water and the title compound is collected which has a melting point of 187° to 194° C. The title compound may then be dissolved in 20 parts of tetrahydrofuran and treated with 1 part of potassium carbonate and 3 parts of water. After stirring for 16 hours the mixture may be diluted with 150 parts of water and the title product of Example 3 may be obtained.

EXAMPLE 5

3-Methoxy-19-Norprega-2,5(10),17(20)-Triene-21-Nitrile

To a solution of 913 parts of sodium diethylcyanomethylene phosphonate and 100 parts of tetrahydrofuran is added 5 parts of 1,4-dihydroestrone in 125 parts of the same solvent. After stirring for 16 hours, the solution is diluted with 1,800 parts of water and the crude product is collected. Recrystallization from methylene chloride ethanol solvent system gives the title product which has a melting point of 164.5° C.

EXAMPLE 6

3-Oxo-19-Norpregna-5(10),17(20)-Diene-21-Nitrile

One part of the title compound of Example 5 is suspended in 95 parts of methanol and 0.7 parts of oxalic acid and 10 parts of water is added. After stirring for 1 hour, the solution is diluted with 400 parts of water to yield the title compound having a melting point of 144.5 degrees to 147° C.

EXAMPLE 7

3-Oxo-19-Norpregna-4,9,17(20)-Triene-21-Nitrile

To 1 part of the title compound of Example 6 dissolved in 25 parts of dried pyridine is added 1.2 parts of pyrrolidine hydrotribromide. After stirring for 48 hours, the majority of the solvent is evaporated and 50 parts of methylene chloride is added. The solution is washed successively with 50 parts of a 5 percent hydrochloric acid solution and 5 percent bicarbonate solution and dried with sodium sulfate. After treatment with decolorizing carbon, the solvent is removed and the residue chromatographed on silica using a mixture of 1 part ethyl acetate and 4 parts toluene as a solvent system. After removal of the solvents, the residue is crystallized from a methanol water solvent system to give the title product which has a melting point of 140.5 degrees to 143° C.

EXAMPLE 8

3-Oxo-19-Norpregna-4,9,11,17(20)-Tetraene-21-Nitrile 1 part of acetyl chloride is added to 60 parts of anhydrous methanol at 0° C. Then 1 part of the title compound of Example 7 is added and goes into solution. After one-half hour the mixture is diluted with 50 parts of water to give the 5(10),9(11)-dienone having a melting point of 150° to 155° C. One part of the deconjugated compound is dissolved in 50 parts of dioxane and 1.8 parts of recrystallized dichlorodicyanobenzoquinone is added. After stirring at room temperature for 22 hours, the precipitated hydroquinone is filtered and the solvent evaporated. Residue is dissolved in 75 parts of methylene chloride and washed with 100 parts of 2.5 percent sodium bisulfite solution. After separation the organic layer is dried with sodium sulfate and the solvent evaporated. The residue is chromatographed on silica using 15 parts of ethyl acetate and 85 parts of methylene chloride to yield the title product having a melting point 159.5° to 160.5° C. after recrystallization from a methylene chloride methanol solvent system.

EXAMPLE 9

Phenylmethyl 3-(Acetyloxy)-20-Cyano-19-Norpregna-5,17(20)-Dien-21-Oate 3.8 parts of 19-nor-dehydroisoandrosterone acetate in a mixture of 60 parts of benzene, 50 parts of acetic acid, 4.2 parts of benzylcyanoacetate and 3 parts of ammonium acetate is refluxed for 16 hours. After cooling, the mixture is diluted with 250 parts of toluene and washed 3 times with water. After drying with sodium sulfate, the solvent is evaporated and the residue crystallized from methanol to yield the title compound having a melting point of 155° C.

EXAMPLE 10

Phenylmethyl 20-Cyano-3-Hydroxy-19-Norpregna-5,17(20)-Diene-21-Oate 5 parts of the title compound of Example 9 is transesterified with 125 parts of ethanol and 125 parts of toluene containing 2 parts of p-toluenesulfonic acid monohydrate. After refluxing for 12 hours, 2 parts of pyridine is added and the solvents removed. Residue is crystallized from methanol water to yield the title product which has a melting point of 104° to 109° C.

EXAMPLE 11

Phenylmethyl 20-Cyano-3-Oxo-19-Norpregna-4,17(20)-Dien-21-Oate

The title compound of Example 10 is oxidized to form the title compound using the modified Oppenauer oxidation described in the preparation of the title compound in Example 2. Title compound has a melting point of 142° to 140° C. like those used in Examples 3 and 4. The title compound may then be hydrogenated in tetrahydrofuran using palladium on strontium carbonate as a catalyst whereby the benzyl group is cleaved and decarboxylation occurs to yield the title compound of Example 2.

EXAMPLE 12

3-Oxo-19-Norpregna-4,17(20)-Diene-21-Nitrile Oxime 1 part of the title compound of Example 11 is suspended in 10 parts of ethanol and then 0.3 parts of hydroxylamine hydrochloride and 5 parts of pyridine is added. After stirring at room temperature for 2 hours, the solution is diluted with water to yield the title compound which has a melting point of 141° C. with decomposition.

EXAMPLE 13

3-Oxo-19-Norpregna-4-Ene-21-Nitrile

To a solution of 22 parts of sodium diethylcyanomethylene phosphonate and 180 parts of tetrohydrofuran, is added 20 parts of the 3-dimethyl ketal of 19-nor-5(10)-androstene-3,17-dione in 200 parts of tetrahydrofuran. After stirring at room temperature for 21 hours, the mixture is poured in water and the granular precipitate collected. The solid is dissolved in 400 parts of methylene chloride treated with a decolorizing charcoal and filtered using filter acid. The solution is diluted with 400 parts of ethanol and the volume reduced to 200 parts. The cyanomethylene ketal which crystallizes upon scratching has a melting point of 145° to 148° C.

1 part of the cyanomethylene ketal is suspended in 40 parts of methanol and 2.9 parts of magnesium is added. The exothermic reaction is moderated with intermittent cooling with a water bath and stirred for 4 hours. Then 25 parts of citric acid in 100 parts of water is added to the gelatinous mixture and the resultant solution is extracted with 200 parts of chloroform in 3 portions. After drying with sodium sulfate, the solvent is removed and the residue chromatographed on silica with 5 parts of ethyl acetate and 95 parts of toluene as a solvent system. The resultant reduced ketal is dissolved in 20 parts of 2 N aqueous hydrochloric acid. After 2 hours the layers are separated and the organic layer washed with 20 parts of 5 percent sodium bicarbonate. After drying over sodium sulfate, the solvent is removed and the residue crystallized from an ether and petroleum ether solvent system to yield the title compound which has a melting point of 115° to 118° C.
CHART A
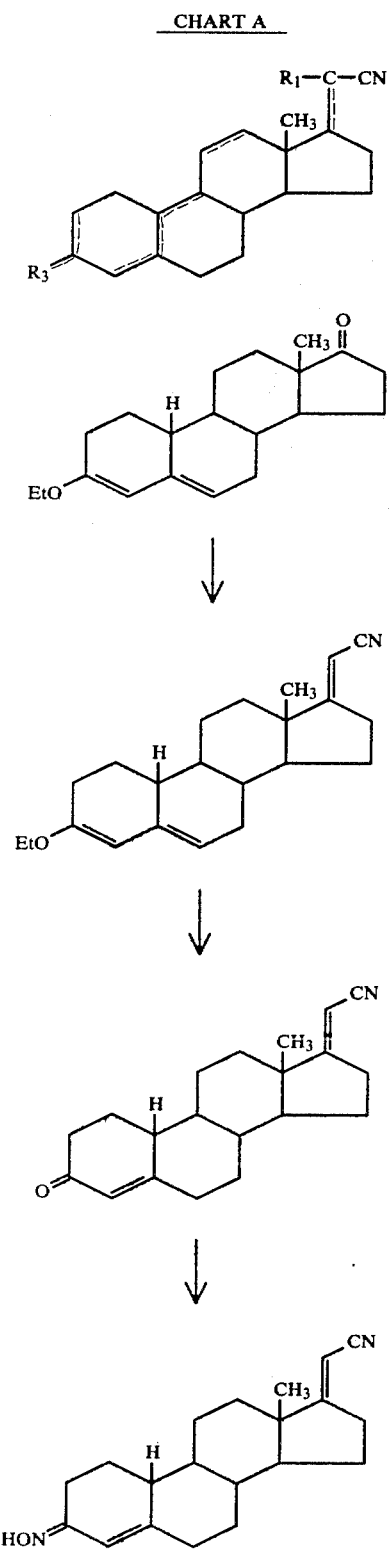
CHART B
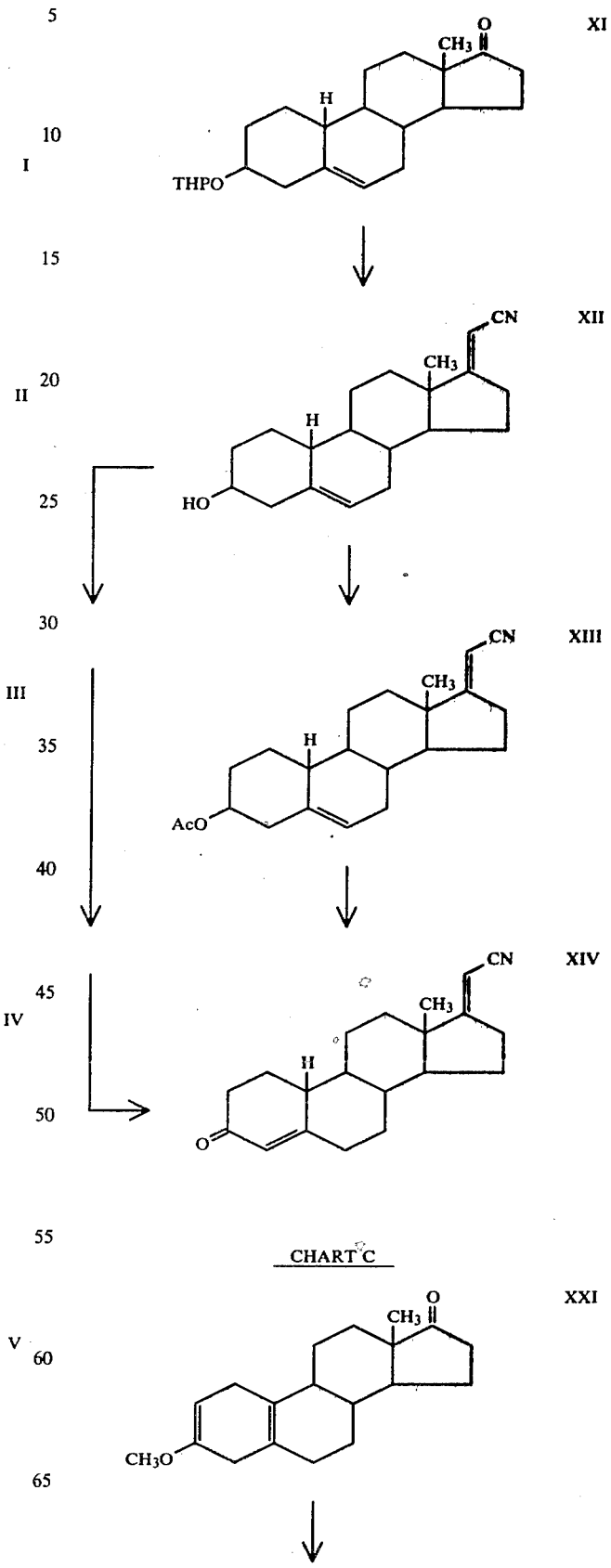
CHART C

CHART C -continued
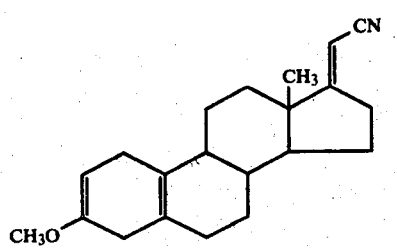 XXII
↓
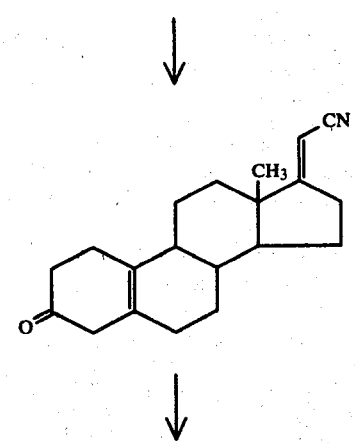 XXIII
↓
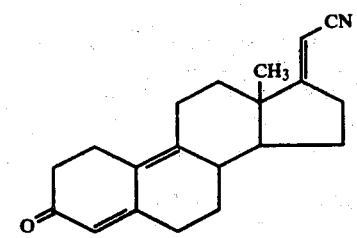 XXIV
↓
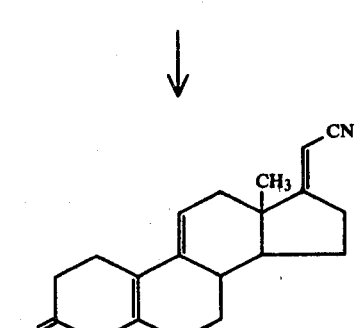 XXV
↓
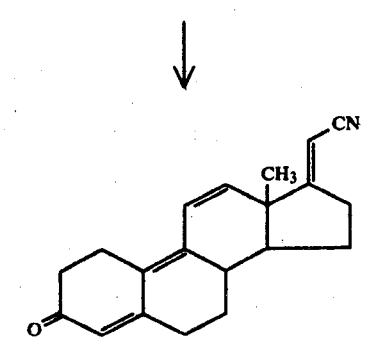 XXVI
CHART D
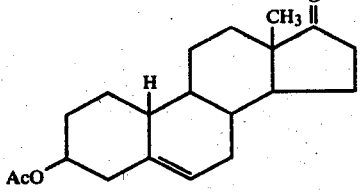 XXXI
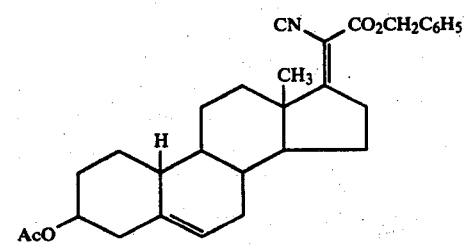 XXXII
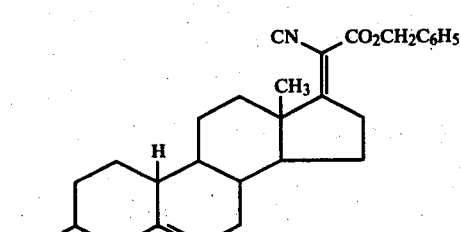 XXXIII
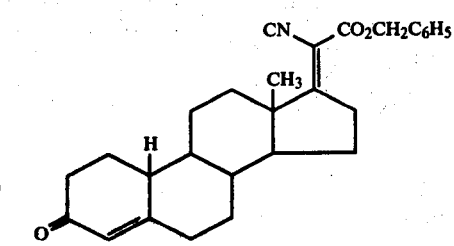 XXXIV
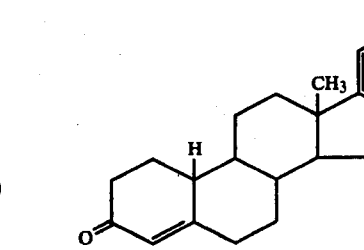 XXXV
CHART E
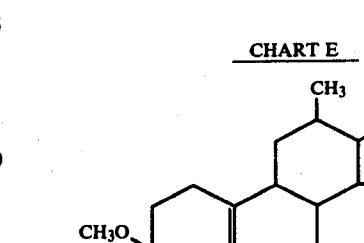 XLI
↓

-continued
CHART E

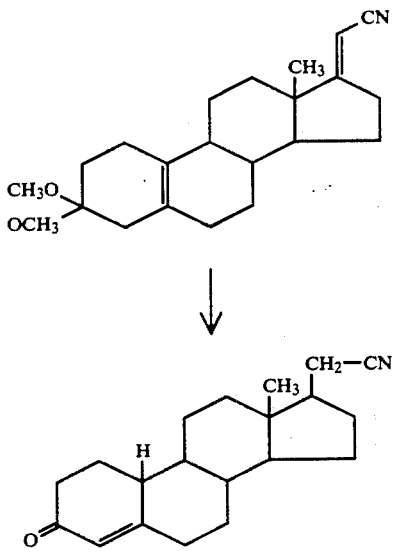

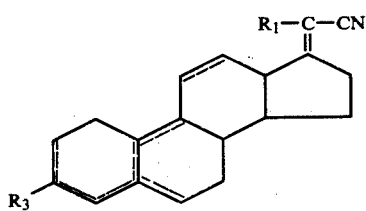

I claim:
1. A compound of the formula:

![structure]

wherein $R_1$ is:
(a) hydrogen;

(b) phenyl alkyl carboxylic acid ester, the alkyl portion having 1 to 6 carbon atoms inclusive;
wherein $R_3$ is
(a) oxo
(b) =NOH;
(c) —$OR_4$; or
(d) —OC=O($R_4$)
wherein $R_4$ is
(a) hydrogen; or
(b) alkyl of 1 to 6 carbon atoms inclusive.

2. 3-Oxo-19-norpregna-4,17(20)-diene-21-nitrile, a compound according to claim 1.

3. Phenylmethyl-20-cyano-3-oxo-19-norpregna-4,17(20)-dien-21-oate, a compound according to claim 1.

4. 3-Oxo-19-norpregna-4,9,17(20)-triene-21-nitrile, a compound according to claim 1.

5. 3-Oxo-19-norpregna-5(10),17(20)-diene-21-nitrile, a compound according to claim 1.

6. 3-Oxo-19-norpregna-4,9,11,17(20)-tetraene-21-nitrile, a compound according to claim 1.

7. A compound according to claim 1 wherein $R_3$ is =NOH.

8. 3-Oxo-19-norpregna-4,17(20)-diene-21-nitrile oxime, a compound according to claim 7.

9. A compound according to claim 1 wherein $R_3$ is —$OR_4$.

10. 3-Ethoxy-19-norpregna-3,5,17(20)-triene-21-nitrile, a compound according to claim 9.

11. Phenylmethyl-20-cyano-3β-hydroxy-19-norpregna-1,5,17(20)-dien-21-oate, a compound according to claim 9.

12. 3-methoxy-19-norpregna-2,5(10),17(20)-triene-21-nitrile, a compound according to claim 9.

13. 3β-hydroxy-19-norpregna-5,17(20)-diene-21-nitrile, a compound according to claim 9.

14. A compound according to claim 1 wherein $R_3$ is —OC=O($R_4$).

15. 3β-(acetyloxy)-19-norpregna-5,17(20)-diene-21-nitrile, a compound according to claim 14.

* * * * *